United States Patent
Mafi et al.

(10) Patent No.: US 8,992,540 B2
(45) Date of Patent: Mar. 31, 2015

(54) ADJUSTABLE SURGICAL INSTRUMENTS AND METHODS OF USE AND FABRICATION

(75) Inventors: Masoumeh Mafi, Mountain View, CA (US); Samuel V. Bolosan, San Jose, CA (US); Ankit K. Mehta, Santa Clara, CA (US)

(73) Assignee: Kyphon Sarl, Neuchatel (CH)

( * ) Notice: Subject to any disclaimer, the term of this patent is extended or adjusted under 35 U.S.C. 154(b) by 669 days.

(21) Appl. No.: 12/841,974

(22) Filed: Jul. 22, 2010

(65) Prior Publication Data

US 2012/0022574 A1 Jan. 26, 2012

(51) Int. Cl.
| | |
|---|---|
| *A61B 17/56* | (2006.01) |
| *A61M 25/10* | (2013.01) |
| *A61B 19/00* | (2006.01) |
| *A61F 2/44* | (2006.01) |
| *A61M 25/00* | (2006.01) |

(52) U.S. Cl.
CPC ........ *A61M 25/10* (2013.01); *A61B 2019/5466* (2013.01); *A61F 2/4455* (2013.01); *A61F 2002/444* (2013.01); *A61M 2025/0008* (2013.01); *A61M 2025/1068* (2013.01)
USPC .......................................................... 606/90

(58) Field of Classification Search
USPC ................................... 606/90, 192; 604/96.01
See application file for complete search history.

(56) References Cited

U.S. PATENT DOCUMENTS

| | | | | |
|---|---|---|---|---|
| 6,235,043 | B1 * | 5/2001 | Reiley et al. ................... | 606/192 |
| 2003/0060842 | A1 * | 3/2003 | Chin et al. ..................... | 606/170 |
| 2004/0087900 | A1 * | 5/2004 | Thompson et al. ......... | 604/96.01 |
| 2004/0098017 | A1 * | 5/2004 | Saab et al. ..................... | 606/192 |
| 2007/0142915 | A1 * | 6/2007 | Altarac et al. ............. | 623/17.11 |

* cited by examiner

*Primary Examiner* — Christian Sevilla
(74) *Attorney, Agent, or Firm* — Leo G. Lenna; Sorell, Lenna & Schmidt LLP

(57) ABSTRACT

A system for assessing an intervertebral disc space comprises an elongated catheter with proximal and distal ends and an expandable body carried at the distal end of the elongated catheter. The expandable body includes a distal cap portion. The system further includes a mandrel extending through the elongated catheter and the expandable body and attached to the distal cap portion. The mandrel is movable within the elongated catheter and the expandable body to reposition the distal cap portion relative to the distal end of the elongated catheter while the expandable body is positioned within the intervertebral disc space.

23 Claims, 4 Drawing Sheets

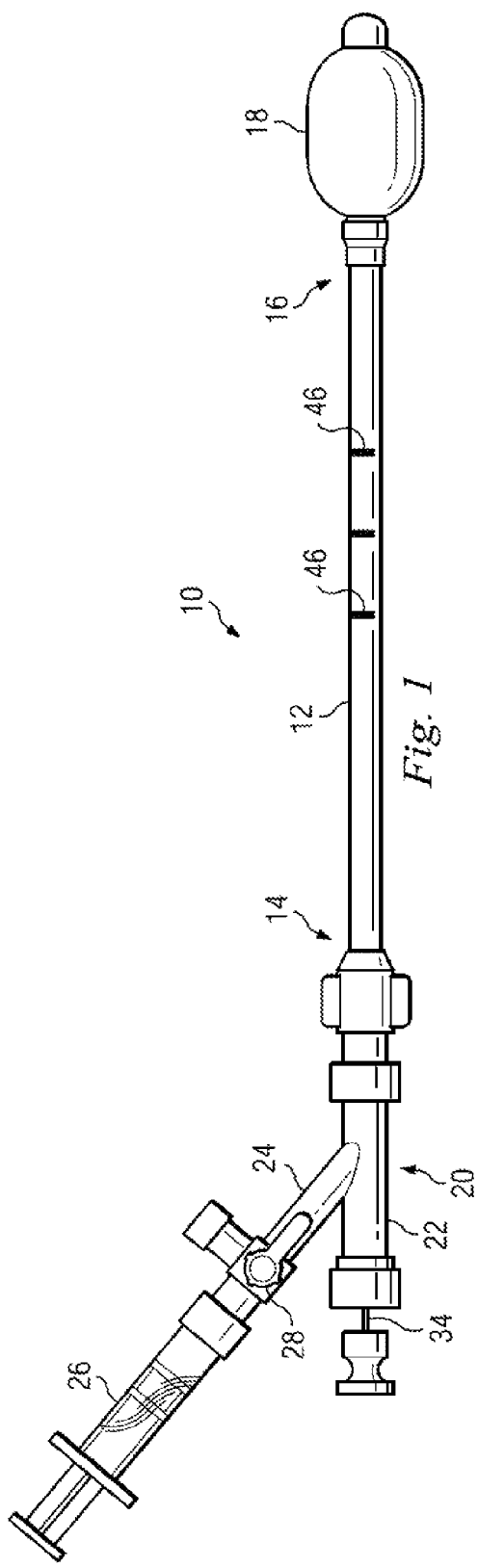
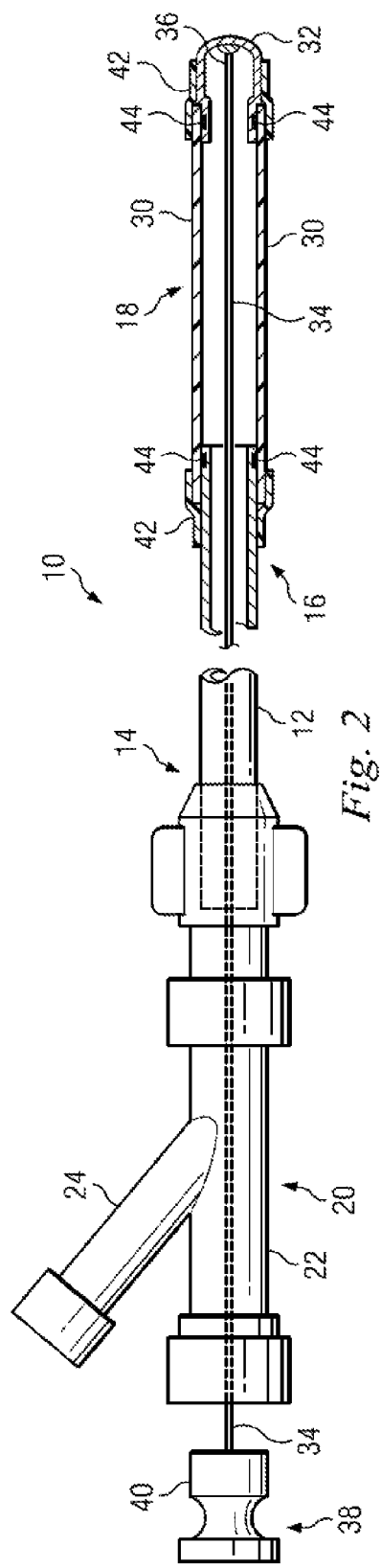

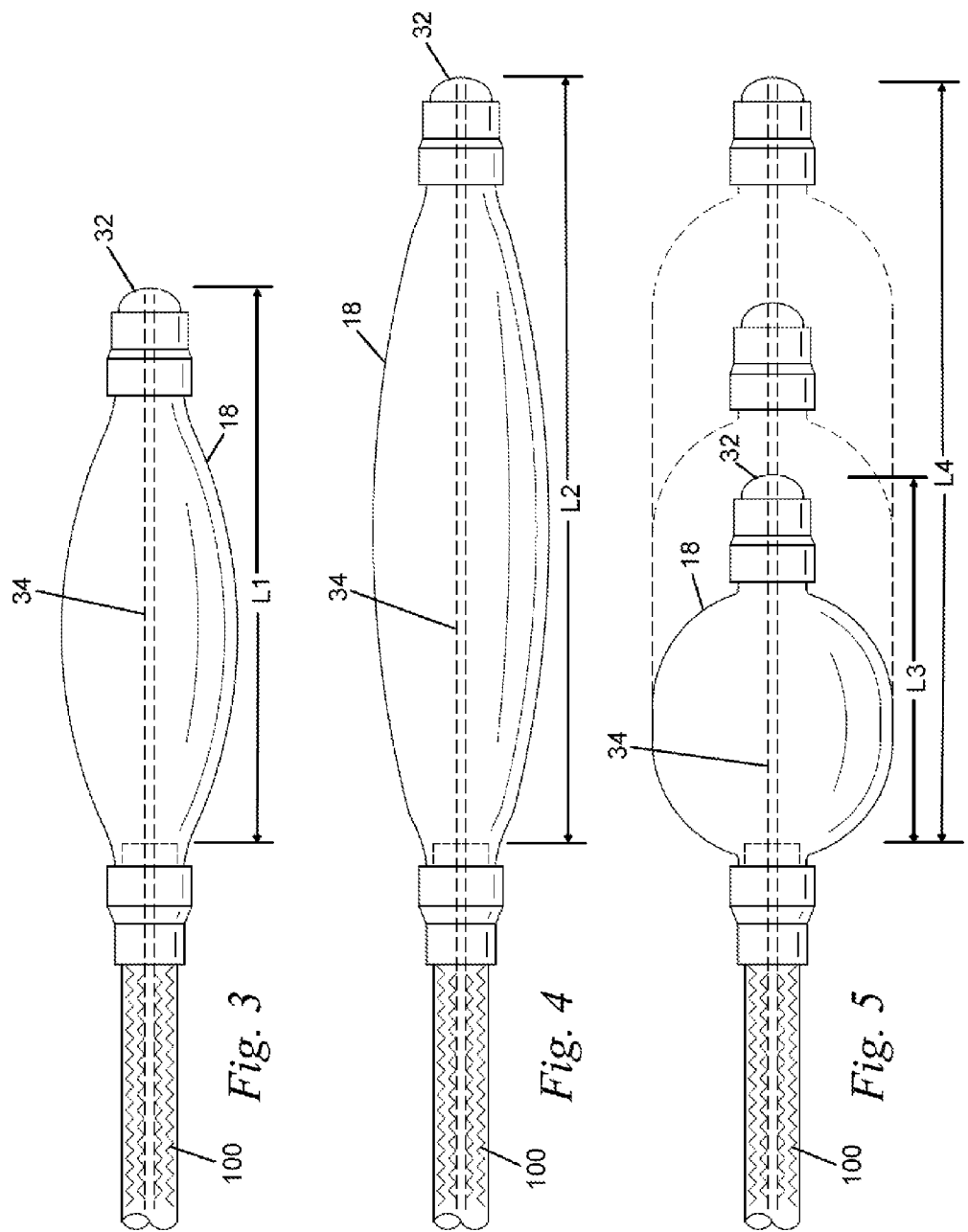

ADJUSTABLE SURGICAL INSTRUMENTS AND METHODS OF USE AND FABRICATION

BACKGROUND

Degenerated disc disease refers to a syndrome in which a compromised disc causes low back pain. Disc degeneration may result in disc herniation in which the central portion of the intervertebral disc, known as the nucleus pulposus, may protrude through an opening in the surrounding fibrous ring, known as the annulus fibrous. A herniated lumbar disc can push on spinal nerves causing severe, shooting, leg pain, numbness, and/or weakness. Discectomy is a surgical procedure in which the nucleus pulposus of a herniated intervertebral disc is resected or removed to relieve pressure on the spinal cord and radiating nerves. Improved tools are needed to allow physicians to evaluate the extent of discectomy that has been performed and to assess the intradiscal space for further procedures such as fusion or arthroplasty.

SUMMARY

In one embodiment of the present disclosure, a system for assessing an intervertebral disc space comprises an elongated catheter with proximal and distal ends and an expandable body carried at the distal end of the elongated catheter. The expandable body includes a distal cap portion. The system further includes a mandrel extending through the elongated catheter and the expandable body and attached to the distal cap portion. The mandrel is movable within the elongated catheter and the expandable body to reposition the distal cap portion relative to the distal end of the elongated catheter while the expandable body is positioned within the intervertebral disc space.

In another embodiment of the present disclosure, a method for assessing an intervertebral disc space comprises selecting an assessment instrument. The assessment instrument includes an elongated catheter with proximal and distal ends and an expandable body carried at the distal end of the elongated catheter. The expandable body includes a distal cap portion. The instrument further includes a mandrel extending through the elongated catheter and the expandable body and attached to the distal cap portion. The method further includes inserting the expandable body into the intervertebral disc space, extending the mandrel to move the distal cap portion distally of the distal end of the elongated catheter, and expanding the expandable body within the intervertebral disc space.

In another embodiment of the present disclosure, a system for assessing an intervertebral disc space comprises an elongated catheter with a central lumen extending between distal and proximal end portions of the elongated catheter and an expandable body carried at the distal end portion of the elongated catheter. The expandable body includes a distal tip. The system further comprises a mandrel sized to extend through the lumen and the expandable body. The mandrel includes a distal end fixedly attached to the distal tip of the expandable body and a proximal end extending proximally of the proximal end portion of the elongated catheter and including a gripping section. The expandable body has a first length when the gripping section is in a first position relative to the proximal end portion of the elongated catheter and has a second length, longer than the first length, when the gripping section is in a second position, closer to the proximal end portion of the elongated catheter than when in the first position.

Further aspects, forms, embodiments, objects, features, benefits, and advantages of the present invention shall become apparent from the detailed drawings and descriptions provided herein.

BRIEF DESCRIPTION OF THE DRAWINGS

FIG. 1 illustrates a medical device for intervertebral disc assessment according to one embodiment of this disclosure.

FIG. 2 illustrates a partial cross-sectional view of the medical device of FIG. 1.

FIG. 3 illustrates an expandable portion of the medical device of FIG. 1 disposed in an extended configuration.

FIG. 4 illustrates an expandable portion of the medical device of FIG. 1 disposed in a different extended configuration.

FIG. 5 illustrates an expandable portion of the medical device of FIG. 1 disposed in different expanded and extended configurations.

DETAILED DESCRIPTION

Figure 6:
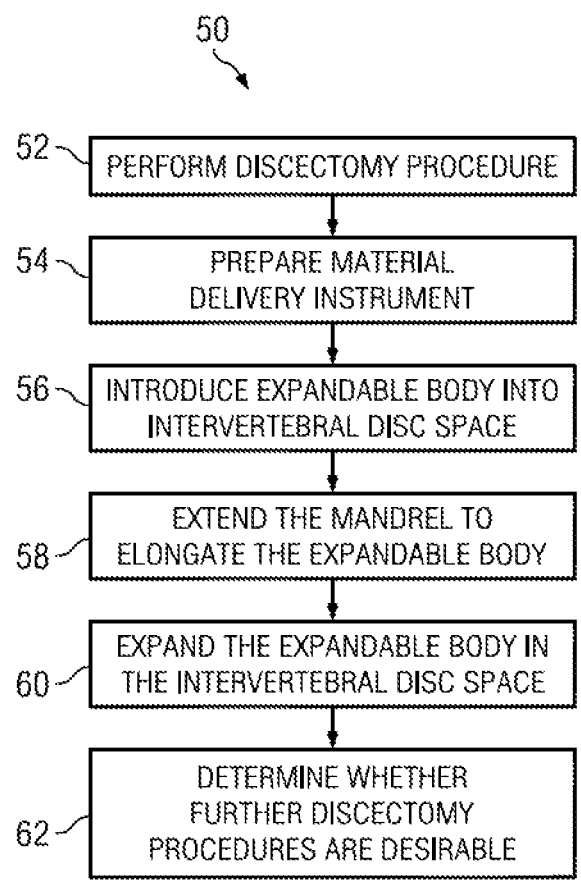
FIG. 6 describes a surgical method according to one embodiment of this disclosure.

The present disclosure relates generally to the field of intervertebral disc treatment, and more particularly to systems and methods for evaluating an intervertebral disc space in conjunction with a discectomy procedure. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Referring first to FIG. 1, a medical device for intervertebral disc assessment and treatment is indicated generally by the numeral 10. The device 10 includes a catheter 12 having a proximal end 14 and a distal end 16. A lumen extends through the catheter between the ends 14, 16. An expandable body 18 is carried by the distal end 16 of the catheter and a connection assembly 20 is carried by the proximal end 14 of the catheter.

In this embodiment, the connection assembly 20 is a Y-port connection assembly with a tubular section 22 coaxially aligned with the catheter 12 and a tubular section 24 obliquely intersecting the tubular section 22. The tubular section 22 is connected to a material delivery instrument 26 via an adapter 28. A suitable material delivery instrument may be, for example, a syringe for containing an inflation medium to be delivered to the expandable body 18. The adapter 28, which may be a two-way stopcock, is configured to control the flow of the inflation medium between the material delivery instrument 26 and the catheter 12.

As shown more clearly in FIG. 2, the expandable body 18 comprises an expandable tube 30 connected to and extending between the distal end 16 of the catheter 12 and a cap portion 32. As will be described in greater detail below, the cap portion 32 may be bonded to the expandable tube 30, but in alternative embodiments, the cap portion may be an integrally formed closed distal tip or a self-sealed distal tip of an expandable tube or balloon.

A mandrel 34, having a distal end 36 and a proximal end 38, extends through the expandable tube 30, the lumen of catheter 12, and the tubular section 22 of the connection assembly 20. The mandrel 34 is movable generally linearly along an axis defined through those components of the device 10. The distal end 36 of the mandrel 34 is connected to the cap portion 32, and the proximal end 38 is fitted with a handle 40. The connection between the distal end 36 of the mandrel 34 and the cap portion 32 may be a fixed connection using, for example, an adhesive, a weld, a mechanical connection, or other type of rigid bond. In certain embodiments, an ultraviolet light activated glue may be a suitable adhesive. In alternative embodiments, the mandrel and cap portion may be connected by other types of connections which allow the distal end 36 of the mandrel 34 to remain attached to the cap portion 32 while the mandrel is both extended and retracted within the catheter 12. Other types of suitable connections may include a movable joint, including for example, a ball-in-socket joint or a disconnectable joint such as a threaded connection. In embodiments where the cap portion is an integrally formed distal tip of the expandable body, the mandrel may be attached directly to a distal surface of the expandable body.

The mandrel 34 may be formed from a material sufficiently rigid to control movement of the cap portion 32 within uninflated, underinflated, and fully inflated expandable bodies. A suitable mandrel material may be, for example, 0.025 in. stainless steel wire. The mandrel may, alternatively, be formed from a tubular member. As shown in FIGS. 3-5, the mandrel 34 may be used to adjust the length of the expandable body 18. FIG. 3, for example, depicts an underinflated expandable body 18 having a length L1 between the distal end of the catheter 12 and cap portion 32. Sliding the mandrel 18 moves the cap portion 32 further away from the distal end of the catheter 12 and elongates the expandable body 18 to a length L2 as shown in FIG. 4. The elongation of the expandable body 18 may occur by stretching, unfolding, unrolling, or any other method of lengthening the expandable body.

As shown in FIG. 5, the mandrel 34 may slide within the catheter 12 and be used to selectively adjust the length of the inflated expandable body 18 to assess space within a body cavity. For example, the expandable body 18 may have a length L3 of approximately 10 mm prior to elongation with the mandrel. The mandrel 34 may be used to lengthen the expandable body 18 to an extended length L4 which may be approximately 65 mm or greater. Thus, in some embodiments, the use of the mandrel may elongate the expandable body between 0 and 55 mm. It is understood that mandrels and their associated expandable bodies may be provided in a variety of sizes, and the dimensions provided are mere examples. As will be described in greater detail below, the size of the intervertebral disc space and the size of a cavity created by prior discectomy procedures may limit the extension of the mandrel and the length of the expandable body.

Suitable materials may be selected for the fabrication of the components of the disc assessment device 10. The catheter may have a shaft that is flexible and resistant to kink formation. The materials for the catheter may also be selected to facilitate advancement of the expandable body. The catheter can be constructed, for example, using standard flexible, medical grade plastic materials, like vinyl, nylon, polyethylenes, ionomer, polyurethane, polytetrafluoroethylene (PTFE), polyetheretherketone (PEEK), and/or polyethylene tetraphthalate (PET). An elastomeric material, polyether block amide, which is offered by Arkema of Puteaux, France under the tradename Pebax may be suitable for some embodiments. The catheter can also be fabricated from more rigid materials to impart greater stiffness and thereby aid in its manipulation. More rigid materials that can be used for this purpose include stainless steel, nickel-titanium alloys, and other metal alloys. The catheter may also be constructed using braided or woven materials to impart greater stiffness and withstand torque.

The expandable tube may be formed of a highly compliant, elastomeric material capable of generally conforming to surrounding tissue when the expandable body 18 is inflated. Suitable materials may include silicone, latex, polyurethane, or neoprene. In some embodiments, a thermoplastic rubber elastomer offered by AdvanSource Biomaterial Corporation of Wilmington, Mass. under the tradename ChronoPrene may be particularly suitable. Alternatively, the expandable tube may be formed of a material, such as vinyl, nylon, or PET, having relatively inelastic properties.

The expandable tube 30 may be attached to the distal end 16 of the catheter 12 and the cap portion 32 using a bonding material 42. For example, the bonding material may be an adhesive, a melt bond material, or flexible, heat shrinkable tubing. A suitable bonding material may be, for example, heat-shrinkable tubing offered by Tyco Electronics Corporation of Berwyn, Pa. under the tradename Altera MT5000. Although a single bonding material may be used to bond the catheter 12 to the expandable tube 30, more than one bonding material may provide greater adherence. For example, the use of a medical grade adhesive applied between the tube and the catheter together with an externally applied shrink tubing may provide improved gripping force. Medical grade adhesive may also be applied at the proximal and distal edges of the expandable tube 30 to minimize slipping of the bonding material 42. Suitable medical grade adhesive may include products that cure in the presence of ultraviolet light.

To permit radiographic positioning of the expandable body 18, radiopaque markers 44 (FIG. 2) may be applied to the expandable body or the catheter. The markers 44 may be bands secured to the catheter 12 and/or cap portion 32 by crimping, swaging, or other techniques known in the art. A platinum-iridium alloy may be a suitable material for fabricating radiopaque markers. To aid the in the positioning of the expandable body 18 without the fluoroscopic guidance, distance markers 46 may be printed or otherwise formed on the catheter 12 to permit visual monitoring of the catheter insertion depth.

Figure 7:
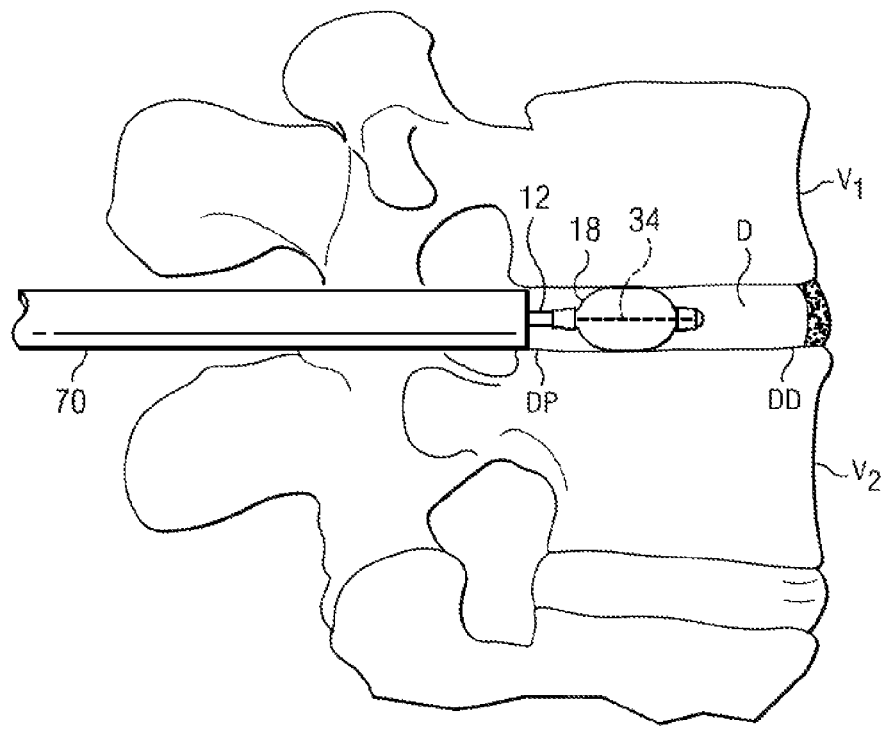
FIGS. 7-8 illustrate deployment of a medical device according to an embodiment of this disclosure.
Figure 8:
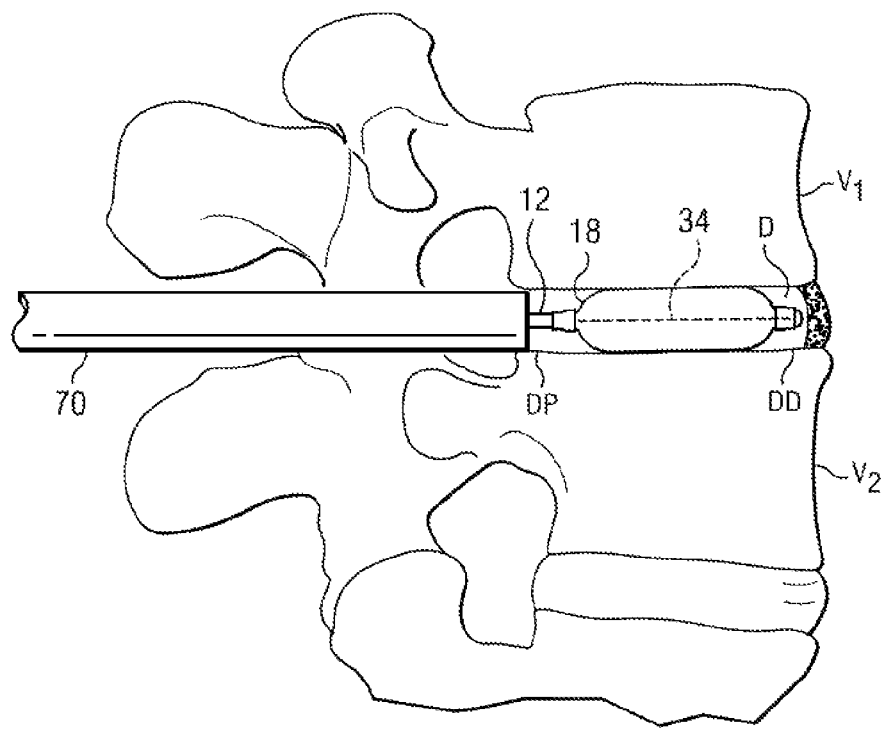

As described in FIG. 6, the device 10 may be used by a practitioner to assess space within an intervertebral disc according to the method 50. At step 52, a conventional discectomy procedure may be performed to remove all or a portion of a nucleus pulposus from an intervertebral disc space D located between vertebral bodies V1 and V2 (FIGS. 7-8). The disc space D may have a distal region DD and a proximal region DP relative to an access location. To determine if further discectomy is needed and to determine the location for any additional discectomy, the disc assessment device 10 may be used.

At step 54, the material delivery instrument 26 may be prepared. For example, an empty 20 cc locking syringe may be attached via luer lock to the stopcock 28. The stopcock 28 may be attached to the tubular section 24 of the connection assembly 20, also via a luer lock connection. Optionally, the expandable body 18 and catheter 12 may be vacuumed prior to use or flushed with inflation medium to eliminate or minimize air bubbles when inflation medium is later added to inflate the expandable body. The stopcock 28 may be used to retain the vacuum the expandable body 18 and catheter 12 while the syringe 26 is detached and filled with an inflation medium such as radiopaque contrast media. The syringe 26 may be reattached to the stopcock 28.

At step 56, the expandable body 18 and catheter 12 may be introduced into a cannula 70 which provides access to the intervertebral disc space D located between vertebral bodies V1 and V2. In this embodiment, a percutaneous and unilateral access technique is used, but in alternative embodiments an open procedure or multilateral approach may be used. The placement of the expandable body 18 and the catheter 12 may be guided by fluoroscopy.

At step 58, the mandrel 34 may be extended to move the cap portion 32 toward the distal area DD of the intervertebral disc space D while a portion of the expandable body 18 remains near the proximal area DP of the intervertebral disc space. To extend the mandrel 34 and elongate the expandable body 18, the practitioner may grip the handle 40 and push it toward the proximal end 14 of the catheter 12. The mandrel 34 may be extended until the practitioner senses contact with tissue or fluoroscopically visualizes sufficient elongation of the expandable body 18. As the mandrel is extended, the expandable body may stretch, unroll, unfold, or otherwise become elongated. The mandrel may extend linearly, generally along an axis defined through the catheter lumen.

The mandrel may be freely slidable within the catheter as described, but in alternative embodiments, the movement of the mandrel may be more discrete or controlled. For example, the mandrel may be configured to threadably engage the catheter so that rotation of the handle advances the mandrel and elongates the expandable body. In another alternative, the mandrel may be advanced along ratchet positions which serve to control the linear movement and of the mandrel, schematically shown as 100.

At step 60, the expandable body 18 is then gradually inflated under fluoroscopy using radiopaque contrast media. The practitioner may detect increasing resistance to inflation as the expandable body 18 expands and may stop further inflation when the expandable body 18 contacts the tissue remaining in the disc space D after the discectomy.

At step 62, the practitioner may assess whether further discectomy is necessary. Under fluoroscopy, the practitioner may determine whether the sufficient discectomy has been performed by determining whether the expandable body 18, in the inflated condition, contacts the endplates of the superior and inferior vertebral bodies and whether the expandable body has inflated past the midline of the contralateral portion of the disc. The discectomy and assessment procedures may be repeated until the practitioner is satisfied with the extent of discectomy. After final assessment is performed, the practitioner may compare the initial volume of the inflation media in the material delivery instrument 26 prior to expansion with the final volume of the inflation media in the material delivery instrument after expansion. The difference in volumes can be used to provide a volumetric estimate of the extent of the discectomy procedure which can be used to determine the amount of bone graft or other filling material to be implanted for fusion.

As described, the mandrel 34 may be extended to elongate the expandable body 18 prior to expansion. Alternatively, as shown in FIGS. 7-8, the mandrel 34 may be extended toward the distal area DD of the disc space D while the expandable body 18 is partially or fully inflated, until the expanded expandable body substantially fills the disc space.

It is understood that the device 10 is not limited to use within an intervertebral disc space, but could be used to assess the size and configuration of cavities in other regions of a body including regions within vasculature, organs, other soft tissue, or bone, including a vertebral body.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. In the claims, means-plus-function clauses are intended to cover the structures described herein as performing the recited function and not only structural equivalents, but also equivalent structures.

What is claimed is:

1. A system for assessing an intervertebral disc space comprising:
    an elongated catheter with proximal and distal ends;
    an expandable body carried at the distal end of the elongated catheter and including a distal cap portion;
    a mandrel extending through the elongated catheter and the expandable body and fixedly attached to the distal cap portion such that the mandrel is configured to adjust a length of the expandable body by movement of the distal cap portion in a first direction to increase a distance between the distal end of the elongated catheter and the distal cap portion from a first distance to a second distance when the expandable body is in an uninflated state and maintain the second distance between the distal end of the elongated catheter and the distal cap portion when the expandable body is in an inflated state,
    wherein the mandrel is movable within the elongated catheter and the expandable body to reposition the distal cap portion relative to the distal end of the elongated catheter while the expandable body is positioned within the intervertebral disc space.

2. The system of claim 1 wherein the mandrel is fixedly attached to the distal cap portion forming a rigid bond.

3. The system of claim 1 wherein the mandrel is movable within the elongated catheter during expansion of the expandable body from the uninflated state to the inflated state.

4. The system of claim 1 wherein the expandable body further comprises an expandable tube attached between the distal end of the elongated catheter and the distal cap portion.

5. The system of claim 1 wherein the mandrel includes a handle extending proximally of the proximal end of the catheter.

6. The system of claim 1 wherein the mandrel includes an elongated wire member.

7. The system of claim 1 wherein the mandrel includes an elongated tubular member.

8. The system of claim 1 further including a connection assembly connected to the proximal end of the elongated catheter and comprising a first tubular portion sized to slidably receive a portion of the mandrel and a second tubular portion configured for connection to a material delivery device.

9. The system of claim 1 further including a cannula sized for through passage of the expandable body and at least a portion of the elongated catheter.

10. The system of claim 1 wherein the expandable body includes at least one radiopaque marker located near a proximal end of the expandable body and at least one radiopaque marker located near a distal end of the expandable body, wherein the radiopaque markers are movable relative to one another with the movement of the mandrel.

11. A method for assessing an intervertebral disc space comprising:
selecting a system according to claim 1;
inserting the expandable body into the intervertebral disc space;
extending the mandrel to move the distal cap portion distally of the distal end of the elongated catheter; and
expanding the expandable body within the intervertebral disc space.

12. The method of claim 11 wherein the expandable body further includes a tubular wall and wherein the step of extending the mandrel includes stretching the tubular wall along an axis defined through the elongated catheter.

13. The method of claim 11 wherein the step of extending the mandrel is conducted concurrently with the step of expanding the expandable body.

14. The method of claim 11 further comprising positioning a cannula at an opening to the intervertebral disc space and extending the expandable body and at least a portion of the elongated catheter through the cannula.

15. A system for assessing an intervertebral disc space comprising:
an elongated catheter with a central lumen extending between distal and proximal end portions of the elongated catheter;
an expandable body carried at the distal end portion of the elongated catheter and including a distal tip;
a mandrel sized to extend through the lumen and the expandable body, the mandrel including a distal end fixedly attached to the distal tip of the expandable body and such that the mandrel is configured to adjust a length of the expandable body by movement of the distal tip in a first direction to increase a distance between the distal end portion of the elongated catheter and the distal tip from a first distance to a second distance when the expandable body is in an uninflated state and maintain the second distance between the distal end portion of the elongated catheter and the distal tip when the expandable body is in an inflated state, a proximal end extending proximally of the proximal end portion of the elongated catheter and including a gripping section,
wherein the expandable body has a first length when the gripping section is in a first position relative to the proximal end portion of the elongated catheter and has a second length, longer than the first length, when the gripping section is in a second position.

16. The system of claim 15 wherein the difference between the first and second lengths is greater than 20 mm.

17. The system of claim 15 wherein the difference between the first and second lengths is greater than 50 mm.

18. The system of claim 15 further comprising a connector assembly attached to the proximal end portion of the elongated catheter, the connector assembly including a first tubular portion coaxial with the central lumen and sized for passage of the mandrel therethrough and a second tubular portion disposed at an oblique angle to the first tubular portion and including a fitting sized to connect with a material delivery device.

19. The system of claim 15 wherein the expandable body includes an expandable wall integrally formed with the distal tip.

20. The system of claim 15 wherein the distal tip includes a cap portion and the expandable body further includes an expandable tubular wall bonded between the cap portion and the distal end portion of the elongated catheter.

21. The system of claim 1 wherein the mandrel is connected with the catheter by a ratchet system to selectively control movement of the expandable body.

22. The system of claim 21 wherein the ratchet system is configured to move the mandrel in the first direction and in an opposite second direction to decrease the distance between the distal end of the elongated catheter and the distal cap portion.

23. The system of claim 1 wherein:
the system further comprises a connection assembly comprising an inner surface defining a passageway, the proximal end of the elongated catheter being coupled to the connection assembly; and
the mandrel extends through the passageway such that an entire portion of the mandrel that extends through the passageway is free floating within the passageway.

* * * * *

UNITED STATES PATENT AND TRADEMARK OFFICE
CERTIFICATE OF CORRECTION

Page 1 of 1

PATENT NO. : 8,992,540 B2
APPLICATION NO. : 12/841974
DATED : March 31, 2015
INVENTOR(S) : Mafi et al.

It is certified that error appears in the above-identified patent and that said Letters Patent is hereby corrected as shown below:

On the Title Page, Item (73), delete "Neuchatel" and insert -- Neuchâtel --, therefor.

In the Specification

Column 3, Line 64, delete "tetraphthalate" and insert -- terephthalate --, therefor.

Column 4, Line 66, delete "vacuum" and insert -- vacuum in --, therefor.

In the Claims

Column 8, Line 5, Claim 15, delete "position." and insert -- position, closer to the proximal end portion of the elongated catheter than when in the first position. --, therefor.

Signed and Sealed this
First Day of September, 2015

Michelle K. Lee
*Director of the United States Patent and Trademark Office*